United States Patent
Bernstein

(10) Patent No.: US 7,511,285 B2
(45) Date of Patent: Mar. 31, 2009

(54) METHODS AND APPARATUS FOR BIOMOLECULE IDENTIFICATION

(75) Inventor: Jonathan Bernstein, Medfield, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 359 days.

(21) Appl. No.: 11/182,337

(22) Filed: Jul. 14, 2005

(65) Prior Publication Data

US 2006/0011862 A1 Jan. 19, 2006

Related U.S. Application Data

(60) Provisional application No. 60/588,631, filed on Jul. 16, 2004, provisional application No. 60/624,979, filed on Nov. 3, 2004.

(51) Int. Cl.
*G01J 1/58* (2006.01)
(52) U.S. Cl. .................................. 250/461.2
(58) Field of Classification Search ............... 250/461.2
See application file for complete search history.

(56) References Cited

U.S. PATENT DOCUMENTS

| | | | |
|---|---|---|---|
| 6,210,896 B1 | 4/2001 | Chan | |
| 6,296,810 B1* | 10/2001 | Ulmer | 422/82.07 |
| 6,355,420 B1 | 3/2002 | Chan | |
| 6,403,311 B1 | 6/2002 | Chan | |
| 6,790,671 B1* | 9/2004 | Austin et al. | 436/172 |
| 2001/0002315 A1 | 5/2001 | Schultz et al. | |
| 2002/0074513 A1* | 6/2002 | Abel et al. | 250/458.1 |
| 2002/0110818 A1 | 8/2002 | Chan | |
| 2002/0115293 A1 | 8/2002 | Ghodsian | |
| 2002/0160400 A1 | 10/2002 | Lakowicz | |
| 2002/0187074 A1* | 12/2002 | O'Connor et al. | 422/82.05 |
| 2003/0017609 A1* | 1/2003 | Yin et al. | 436/161 |
| 2003/0226604 A1* | 12/2003 | Schlautmann et al. | 137/827 |
| 2003/0228682 A1 | 12/2003 | Lakowicz et al. | |
| 2004/0038408 A1* | 2/2004 | Abbott et al. | 436/4 |
| 2004/0046128 A1* | 3/2004 | Abel et al. | 250/458.1 |
| 2004/0148777 A1* | 8/2004 | Sjolander et al. | 29/890.127 |
| 2005/0053974 A1* | 3/2005 | Lakowicz et al. | 435/6 |
| 2005/0084912 A1 | 4/2005 | Poponin | |
| 2005/0084980 A1* | 4/2005 | Koo et al. | 436/171 |
| 2005/0106740 A1* | 5/2005 | Boyes et al. | 436/86 |
| 2005/0229696 A1* | 10/2005 | Takayama | 73/204.26 |
| 2005/0236033 A1* | 10/2005 | Lawandy | 136/252 |
| 2005/0238286 A1* | 10/2005 | Lawandy | 385/39 |
| 2005/0239048 A1* | 10/2005 | Lawandy | 435/4 |
| 2007/0116882 A1* | 5/2007 | Chan et al. | 427/430.1 |

OTHER PUBLICATIONS

Thio, T. et al. Enhanced light transmission through a single subwavelength aperture. Optics Letters. 26:24, 1972-74 (Dec. 2001).
Thio, T. et al. Giant optical transmission of sub-wavelength apertures: physics and applications. Nanotechnology 13, 429-32 (2002).

(Continued)

*Primary Examiner*—David P Porta
*Assistant Examiner*—Djura Malevic
(74) *Attorney, Agent, or Firm*—Ropes & Gray LLP

(57) ABSTRACT

The apparatus and methods described herein provide improved resolution, high-throughput, biomolecule identification by exciting sub-wavelength regions of biomolecules drawn through a microfluidic channel.

58 Claims, 16 Drawing Sheets

OTHER PUBLICATIONS

Xie, X.S. et al. Probing Single Molecule Dynamics. Science. 265, 361-64. (Jul. 15, 1994).

Levene, M.J. et al. Zero-Mode Waveguides for Single Molecule Analysis at High Concentrations. Science. 299, 682-86 (Jan. 31, 2003).

Hayazawa, N. et al. Evanescent field excitation and measurement of dye fluorescence in a metallic probe near-field scanning optical microscope. Journal of Microscopy. 194, 472-76 (May/Jun. 1999).

Hayazawa, N. et al. Metallized tip amplification of near-field Raman scattering. Optics Communications. 183, 333-36 (2000).

Fischer, U. et al. "Controlling Light Confinement by Excitation of Localized Surface Plasmons," in "Near-Field Optics and Surface Plasmom Polaritons," S. Kawata (Ed.), pp. 52-56. Springer-Verlag (2001).

Brongersma, M.L. et al. Electromagnetic Energy Transfer and Switching in Nanoparticle Chain Arrays Below the Diffraction Limit. Physical Review B, published on Dec. 15, 2000.

Maier, S.A. et al. Observation of Near-Field Coupling in Metal Nanoparticle Chains Using Far-Field Polarization Spectroscopy. Physical Review B, published on May 13, 2002.

* cited by examiner

METHODS AND APPARATUS FOR BIOMOLECULE IDENTIFICATION

RELATED APPLICATIONS

This application claims priority under 35 U.S.C. § 119(e) to U.S. Provisional Application Ser. No. 60/588,631, entitled "DNA Sequencing Device," filed Jul. 16, 2004, and U.S. Provisional Application Ser. No. 60/624,979, entitled "Bio-Molecular Identification Chip," filed Nov. 3, 2004, the entirety of which are hereby incorporated by reference.

FIELD OF THE INVENTION

The invention relates generally to the field of molecular identification, and more specifically to apparatus, systems, and methods for identifying biomolecules.

BACKGROUND OF THE INVENTION

Methods and apparatus for accurate and efficient sequencing of biomolecules, such as DNA, RNA, and proteins have long been sought. Knowledge of the exact sequence of biomolecules can be used in the search for cures for diseases and other ailments. Prior methods, however, have failed to provide desirable accuracy and throughput rates. In many applications such as diagnostic medicine and bio-defense, it is possible or even desirable to uniquely identify biomolecules without knowledge of every base-pair (i.e. complete sequencing data).

SUMMARY OF THE INVENTION

In one aspect, this application provides methods and apparatus for high-throughput identification of biomolecules. The biomolecules include but are not limited to polymeric biomolecules such as for examples nucleic acid sequences, DNA and/or RNA, proteins, polypeptides, enzymes, antibodies, aptamers etc. In one embodiment, the invention relates to an identification device including a channel through which a biomolecule is drawn, a radiation introduction element for illuminating a region of the channel which is smaller than the wavelength of the introduced radiation, a sensor for detecting emissions from the biomolecule in the illuminated region, and a processor for identifying the biomolecule based on the detected emissions.

In one embodiment, the polymeric biomolecules are labeled or tagged for optical detection. Suitable labels for use in the present invention include but are not limited to fluorescent tags and quantum dots (referred to hereinafter collectively as "fluorescent tags"). These can be incorporated into the polymeric biomolecules by methods that are well known in the art, including the use of fluorescently tagged primers or fluorescently tagged chain terminating reagents. The fluorescent tags selected for use in the present invention must be distinguishable one from another based on their excitation and/or emission spectra. In one embodiment, a set of tags could be selected which had overlapping emission spectra (Em1, Em2, Em3 and Em4) but separate and distinguishable excitation spectra (Ex1, Ex2, Ex3, and Ex4). A set of tags could also be selected which had overlapping excitation spectra but separate and distinguishable emission spectra. Alternatively, a set of tags could be selected in which some of the tags have overlapping excitation spectra (Ex1and Ex2) but separate and distinguishable emission spectra (Em1 is distinguishable from Em2); while the others have separate and distinguishable excitation spectra (Ex1, Ex3, and Ex4) but overlapping emission spectra (Em1, Em3 and Em4).

Examples of sets of suitable fluorescent tags, together with the wavelength maximum for the excitation and emission spectra are shown in Table 1. The fluorophores that may be used herein are generally available from Applied Biosystems, Inc. (Foster City, Calif.), Molecular Probes, Inc. (Oregon) and others sources.

TABLE 1

Suitable Fluorescent Dyes

| Fluorescent Dye | Excitation Max (nm) | Emission Max (nm) |
|---|---|---|
| Texas Red X | 599 | 617 |
| Carboxy-X-Rhodamine | 585 | 612 |
| CarboxyFluorescein | 494 | 521 |
| CarboxyTetraMethyl-Rhodamine | 561 | 591 |
| Carboxycyanine 5.0 | 650 | 667 |

In one embodiment, the radiation introduction element includes a sub-wavelength aperture for permitting light into the channel. The aperture may be substantially linear or circular in shape. In another embodiment, the radiation introduction element includes a plasmonic resonance-enhanced sub-wavelength aperture for introducing higher intensity light into the channel. In yet another embodiment, the radiation introduction element includes a plurality of plasmonic resonant elements, such as plasmonic islands or rods for exciting fluorescent tags bound to the biomolecule into emitting light.

In a further embodiment, the identification device includes a plurality of radiation introduction elements. Each radiation introduction element may be selected to excite a particular spectrum of excitation from passing biomolecules.

The identification device may also include a positioning element for ensuring the biomolecule passes through the illuminated region as it is drawn through the channel of the identification device. In one embodiment, the positioning element includes a set of electrodes powered by a voltage source. In another embodiment, the positioning element includes a shelf in the channel, over which the biomolecule must be drawn. In a further embodiment, the positioning element includes a peak in the channel.

In another aspect, the invention relates to an identification method. The identification method, in one embodiment, includes introducing radiation into a sub-wavelength region of a microfluidic channel. A biomolecule is drawn along the microfluidic channel through the illuminated region. A sensor detects emissions from the biomolecule resulting from the passage through the illuminated region, from which the biomolecule is identified.

BRIEF DESCRIPTION OF THE DRAWINGS

Embodiments of the invention will now be described, by way of example only, with reference to the accompanying drawings, in which.

DESCRIPTION OF AN ILLUSTRATIVE EMBODIMENT

Figure 1:
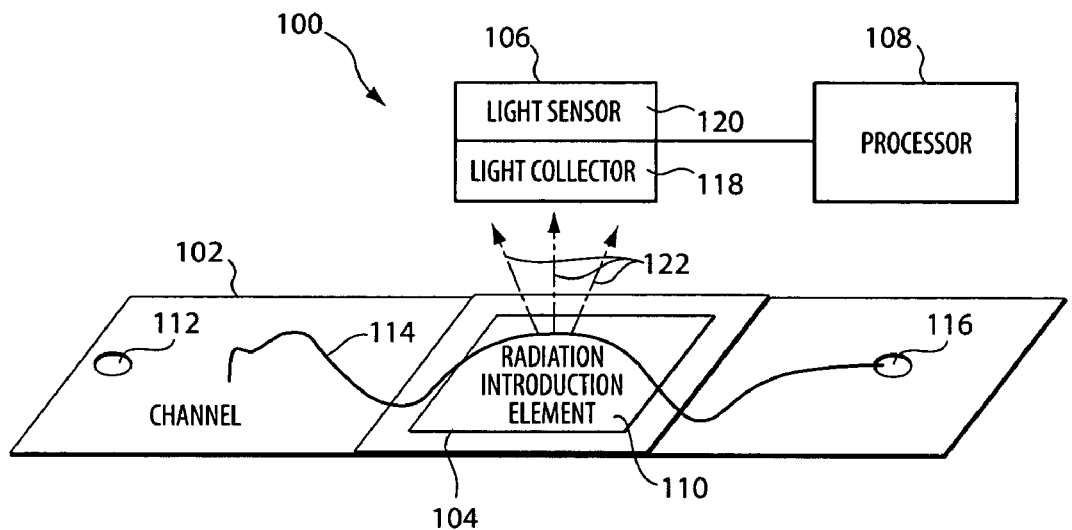
FIG. 1 is a block diagram of an identification device according to an illustrative embodiment of the invention.

To provide an overall understanding of the invention, certain illustrative embodiments will now be described, including apparatus and methods for identifying biomolecules. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope hereof. Throughout the figures, like reference numerals refer to like elements.

FIG. 1 is a block diagram of an identification device 100 according to an illustrative embodiment of the invention. The identification device 100 includes a channel 102, a radiation introduction element 104, a sensor 106, and a processor 108. The identification device may optionally include a positioning element 110.

The channel 102 is preferably formed in a substrate using standard semiconductor processing techniques. In one implementation, the height of the channel is between 0.1 and 10 microns, and the width of the channel is between 1 and 100 microns. However, the height may be greater than 10 microns or less than 0.1 micron. Similarly, the channel, in other implementation may be greater than 100 microns wide or less than 1 micron wide. At one end of the channel 102, an inlet 112 is formed for introducing a biomolecule 114. The biomolecule 114 can be, for example, and without limitation, DNA (either single or double stranded), RNA, or a peptide chain. Preferably, prior to introduction into the channel 102, fluorescent tags have been selectively bound to components of the biomolecule. During operation of the identification device 100, the biomolecule 114 is drawn along the length of the channel to an outlet 116 at the opposite end of the channel 102, for example, by externally applied pressure or electrophoresis.

At a location in the channel 102 between the inlet 112 and the outlet 116, the identification device 100 includes the radiation introduction element 104. The radiation introduction element 104 introduces radiation, for example, light ranging from the ultraviolet end of the electromagnetic spectrum through the visible light spectrum or the infra-red. The radiation introduction element 104 introduces the radiation into a region of the channel 102 which is smaller than the wavelength of the radiation it introduces (referred to herein as the "illuminated region"). Several illustrative implementations of suitable radiation introduction elements 104 are described in further detail below in relation to FIGS. 3-9, and 11.

The identification device 100 includes a sensor 106 for detecting electromagnetic radiation. The sensor 106 includes a light collection element 118 and a light sensor 120. The light collection element 118 may also include an objective lens, preferably with a high numeric aperture. The light collection element 118 may also include and a filter to block light emitted by the radiation introduction element while passing light from the fluorescent tags. The objective lens focuses light 122 from the channel 102 on to the light sensor 120. Alternatively, the light collection element 118 may include a waveguide. The waveguide conducts collected light 122 from the channel 102 to the light detector 120, either directly, or by way of fiber-optic cables. The light sensor 120 can be any device known in the art for detecting and sensing light, for example, a charge-coupled device (CCD) chip.

The sensor 106 is in communication with a processor 108. The processor 108 can be a general or special purpose computer, an application specific processor, a digital signal processor, or a combination thereof. The processor 108 may execute software encoding logic for analyzing the light sensed by the sensor 106 to identify a molecule. Alternatively, such logic can be hardwired into the processor.

The identification device 100 may also optionally include a positioning element 110. The positioning element 100 works to ensure that the biomolecule 114, as it is drawn through the channel 102, passes through the illuminated region created by the radiation introduction element 104. A first illustrative positioning element 110 is described below in relation to FIG.

3. A second illustrative positioning element 110 is described below in relation to FIG. 5. A third illustrative positioning element 110 is described below in relation to FIG. 13, and a fourth illustrative positioning element 110 is described below in relation to FIG. 14.

Figure 2:
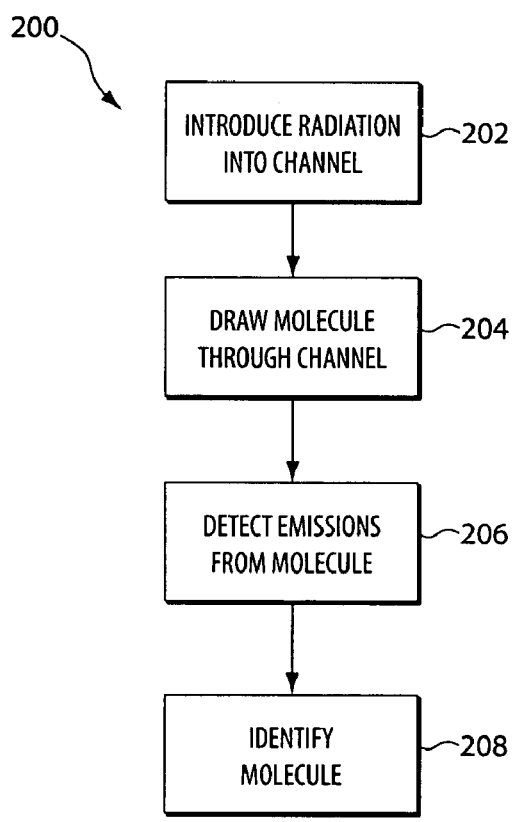
FIG. 2 is a flowchart of a method of identifying a molecule, using, for example, the identification device depicted in FIG. 1, according to an illustrative embodiment of the invention.

FIG. 2 is a flow chart of an illustrative method of identification of a biomolecule (the "identification method 200") using the identification device 100. First, the radiation introduction element 104 introduces radiation into the channel 102 to form the illuminated region (step 202). The size of the illuminated region determines, in part, the resolution with which the identification device can identify components of a biomolecule. For example an illuminated region which is 10 nm across allows the identification device to distinguish fluorescent tags spaced 10 nm apart.

The identification device 100 then draws a biomolecule 114 along the channel 102 (step 204). As mentioned above, the biomolecule 114 is labeled with a plurality of fluorescent tags. Tags of varying excitation spectra are selectively bound to components of the biomolecule 114. For example, with DNA, a different colored tag is attached to molecules which bind to unique, short sequences of base-pairs, typically 3-100 base-pairs long. As the biomolecule 114 passes through the illuminated region, the introduced radiation excites the fluorescent tags bound to the biomolecule, resulting in the emission of a spectra of light 122 corresponding to the illuminated tag. The sensor 106 detects the emitted light 122 (step 206). The processor 108 analyzes the detected light 122, and identifies the component of the biomolecule 114 in the illuminated region based on the spectra of the detected light 122 (step 208).

In alternative implementations, the identification device 100 includes a plurality of radiation introduction elements 104 and sensors 106, spaced at predetermined distances. In one particular implementation, each radiation introduction element 104 introduces the same wavelength of radiation. Alternatively, different radiation introduction elements 104 introduce different wavelengths of radiation. The processor 108 then correlates the detected light emission from each of the sensors 106 to improve molecule identification. Such an identification device 100 is described in further detail in relation to FIGS. 12A-12D.

Figure 3:
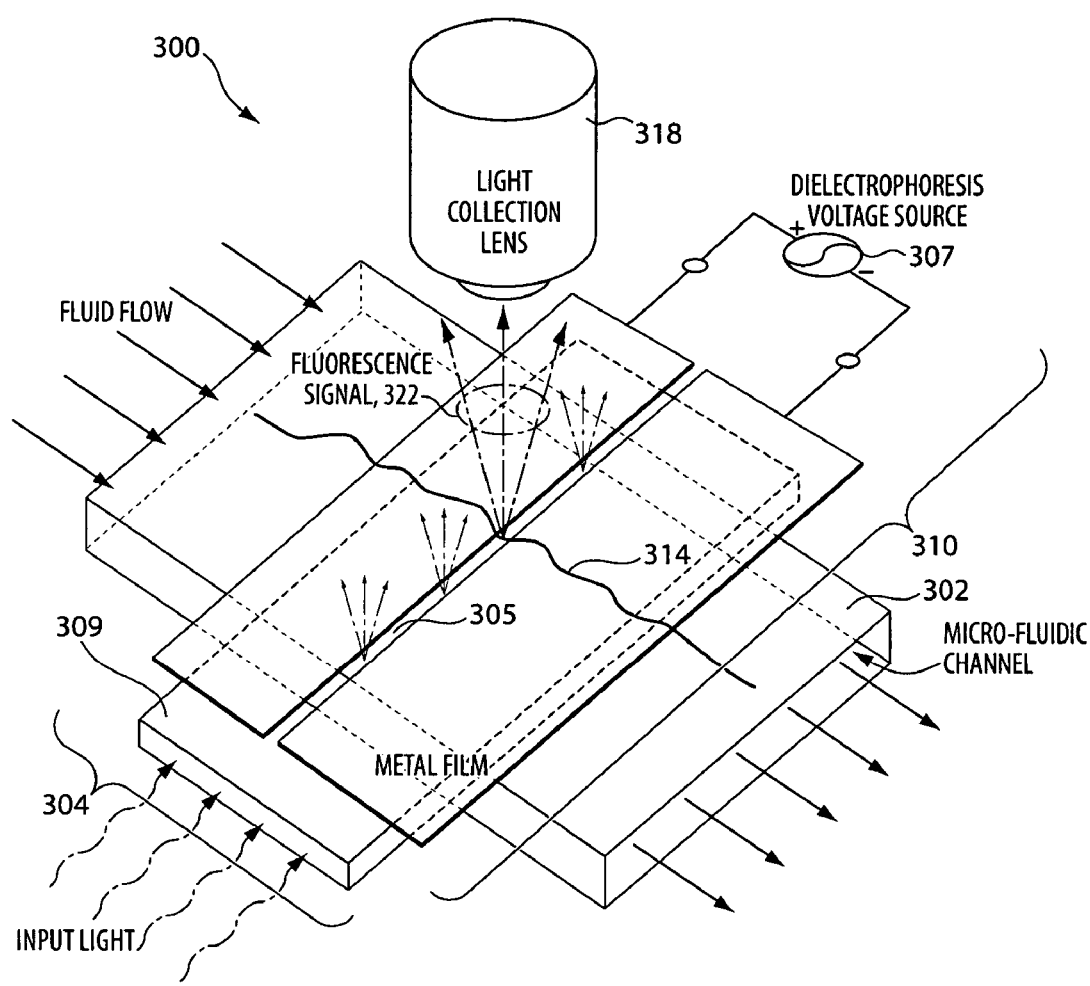
FIG. 3 is a perspective view of a first illustrative embodiment of the identification device of FIG. 1 including a first aperture-based radiation introduction element, according to an illustrative embodiment of the invention.

FIG. 3 is a perspective view of a first illustrative embodiment of the identification device ("identification device 300") of FIG. 1. Identification device 300 includes an aperture-based radiation introduction element 304. That is, the radiation introduction element 304 introduces light into a channel 302 of the identification device 300 through a narrow aperture 305. To generate an illuminated region in the channel 302 which is smaller than the wavelength of the introduced light, the aperture 305 is narrower than the wavelength of the light. The identification device can also operate with an aperture larger than the light wavelength, although with reduced resolution. The aperture is created in a metal film using standard lithography techniques such as e-beam, contact, or UV exposure, combined with plasma etching, ion-beam milling, Focused Ion Beam (FIB) etch, or liftoff. The aperture 305 is preferably about 20 nm wide, though it can be any width that is narrower than the wavelength of the light introduced into the channel 302. The aperture 305 stretches across the entire width of the channel 302.

In the identification device 300, the radiation introduction element 304 is electrified by a voltage source 307 to create an electric field across the aperture 305. As a biomolecule 314 passes through the channel 302, the electric field across the aperture 305 pulls the biomolecule 314 closer to the aperture 305 by electrophoresis or dielectrophoresis, helping to ensure that the biomolecule 314 passes through the illuminated region generated by the radiation introduction element 304. Thus in this implementation, the radiation introduction element 304, in combination with the voltage source 307, serves as a positioning element 310.

Light is introduced into the identification device 300, for passage through the aperture 305, using an optical waveguide 309 running the width of the channel. Light 322 emitted by the biomolecule 314 is collected by an objective lens 318.

Figure 4:
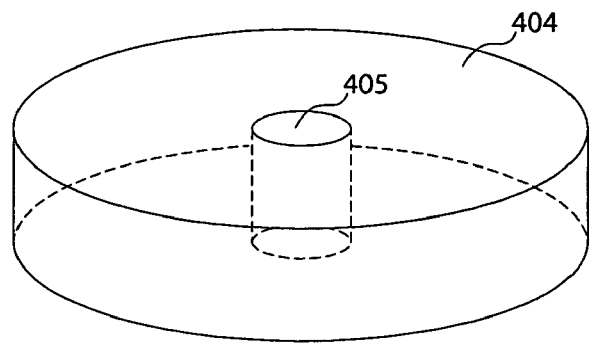
FIG. 4 is a perspective view of a second aperture-based radiation introduction element, according to an illustrative embodiment of the invention.

FIG. 4 is a perspective view of a second aperture-based radiation introduction element 404, according to an illustrative embodiment of the invention. The radiation introduction element 404 includes a generally circular aperture 405 instead of the slot-shaped aperture 305. The aperture 405 has a diameter which is less than the wavelength of the light admitted through the aperture, and is preferably between about 10 nm and about 50 nm.

Figure 5:
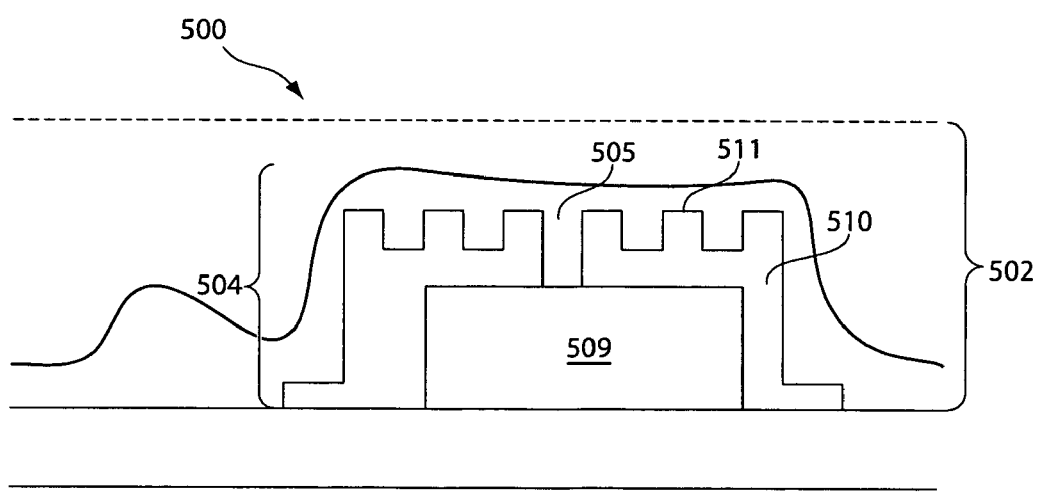
FIG. 5 is a cross-sectional view of a second illustrative embodiment of the identification device of FIG. 1 including a first plasmonic resonance-enhanced aperture-based radiation introduction element, according to an illustrative embodiment of the invention.

FIG. 5 is a cross-sectional view of a second illustrative embodiment of the identification device (the "identification device 500") of FIG. 1 including a first plasmonic resonance-enhanced aperture-based radiation introduction element 504, according to an illustrative embodiment of the invention. Plasmonic resonance refers to the oscillation of free electrons in a metal typically resulting from the excitation of the metal with a light source. With multiple closely spaced metallic features (such as peaks of a grating or individual metallic objects), the oscillation of free electrons within one metallic feature generates an electric field that influences the oscillation of free electrons in the other metallic features. Such influence can result in the free electrons in the metallic features beginning to resonate.

As light passes through an aperture that is smaller than its wavelength, the intensity of the light decreases exponentially in relationship to the width of the aperture. Thus, apertures 305 and 405 of FIGS. 3 and 4 introduce relatively low intensity light into the illuminated region. The intensity is sufficient to identify tagged components, though identification may be somewhat hampered. To increase the intensity of the light in the illuminated region, radiation introduction element 504 includes an evenly spaced grating 511 on either side of a generally slot shaped aperture 505, to generate a plasmonic resonant field across the aperture. The pitch of the grating 511 is less than the wavelength of the light admitted through the aperture 505. Preferably, the pitch is on the order of 20-200 nm.

Figure 6:
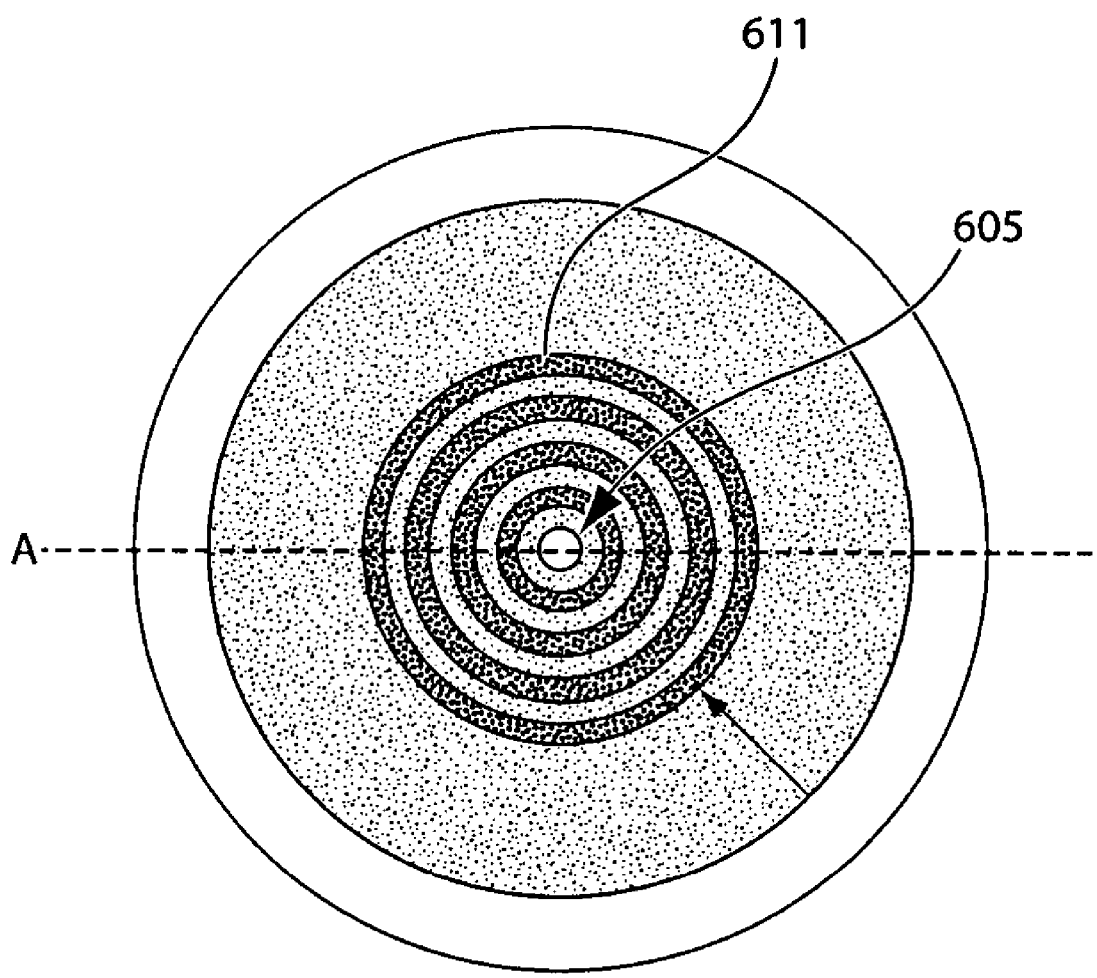
FIG. 6 is a top view of a second plasmonic resonance-enhanced radiation introduction element, according to an illustrative embodiment of the invention.

As light passes through the aperture 505, the light generates a plasmonic resonance across the grating 311, resulting in strong electric field across the aperture 505. The plasmon resonance enhances the intensity of the admitted light, allowing for improved biomolecule identification. The plasmonic resonance light intensification effect is described in further detail in "Enhanced Light Transmission Of Sub-wavelength Apertures: Physics and Applications," by T. Thio et al., published in Optics Letters in 2001, the entirety of which is hereby incorporated by reference. The circular aperture 405 of FIG. 4 can likewise be improved by the incorporation of a grating 611 about the aperture 605, as depicted in FIG. 6.

Referring back to FIG. 5, the radiation introduction element 504 is constructed over an optical waveguide 509. The optical waveguide 509 forms a shelf in the channel 502. The height of the optical waveguide 509 is more than one-half the height of the channel 509. One of ordinary skill will appreciate that the height of the optical waveguide can be between one-eighth the height of the channel to seven-eighth the height of the channel. The combination of the optical waveguide 509 and the radiation introduction element 504 act as a positioning element 510. As a long biomolecule 514 passes over the shelf, the tension from the ends of the biomolecule 514 tend to pull the portion of the biomolecule 514 located on the shelf closer to the aperture 505.

Figure 7:
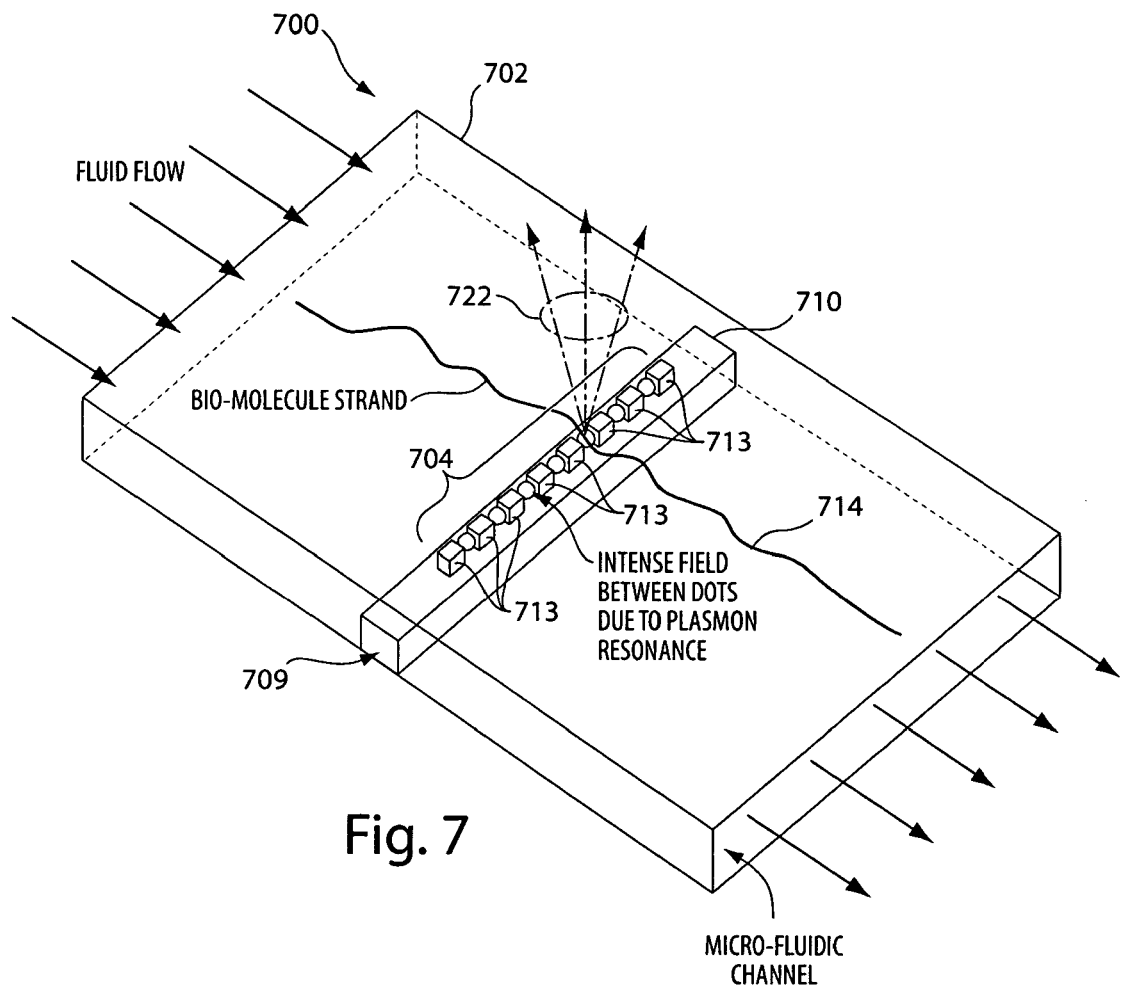
FIG. 7 is a perspective view of a third illustrative embodiment of the identification device of FIG. 1 including a first plasmonic resonance-based radiation introduction element, according to an illustrative embodiment of the invention.

FIG. 7 is a perspective view of a third illustrative embodiment of the identification device of FIG. 1 (the "identification device 700"). In the identification device 700, an illuminated region is created by an apertureless radiation introduction element 704. The radiation introduction element 704 introduces radiation into a channel 702 by exciting plasmonic resonance among a plurality of metallic plasmonic islands 713. These metal islands are preferably in the range of 4-400 nm wide. As a biomolecule 714 passes through the electromagnetic field or fields generated by the excited plasmonic islands (i.e., the illuminated region), the fluorescent tags bound to the biomolecule 714 are excited resulting in the emission of light 722 corresponding to the tag.

These plasmonic islands 713 can be formed of silver, gold, aluminum, or any other metal which can be excited into plasmonic resonance in the visible or near visible portions of the electromagnetic spectrum. In one implementation, the plasmonic islands 713 are spaced periodically across the channel, at, for example, approximately 100 nm, though they may be spaced, without limitation, between 8-400 nm apart. In an alternative implementation, the plasmonic islands are spaced irregularly, thereby resulting in the radiation introduction element 704 generating multiple electromagnetic field frequencies in the illuminated region. The plasmonic islands can be generally circular, polygonal, or irregular in shape.

The plasmonic islands are coupled to a waveguide 709 through which laser light is directed. The laser light can be directed into the waveguide 709 at an angle which results in the total internal reflection of the light as it passes through the waveguide 709. As the laser light reflects off the interface of the waveguide with the plasmonic islands 713, the resulting evanescent field of light escaping into the channel 702 excites the plasmonic islands into resonance. The waveguide 709 can be selected such that the evanescent modes provided by the wave guide 709 are tuned to the plasmonic modes of the plasmonic islands 713, resulting in enhanced resonance. The waveguide can either run the length or the width of the channel 702. As with the waveguide 509 of FIG. 5, if the waveguide 709 runs across the width of the channel 702, it can act as a positioning element 710.

Figure 8:
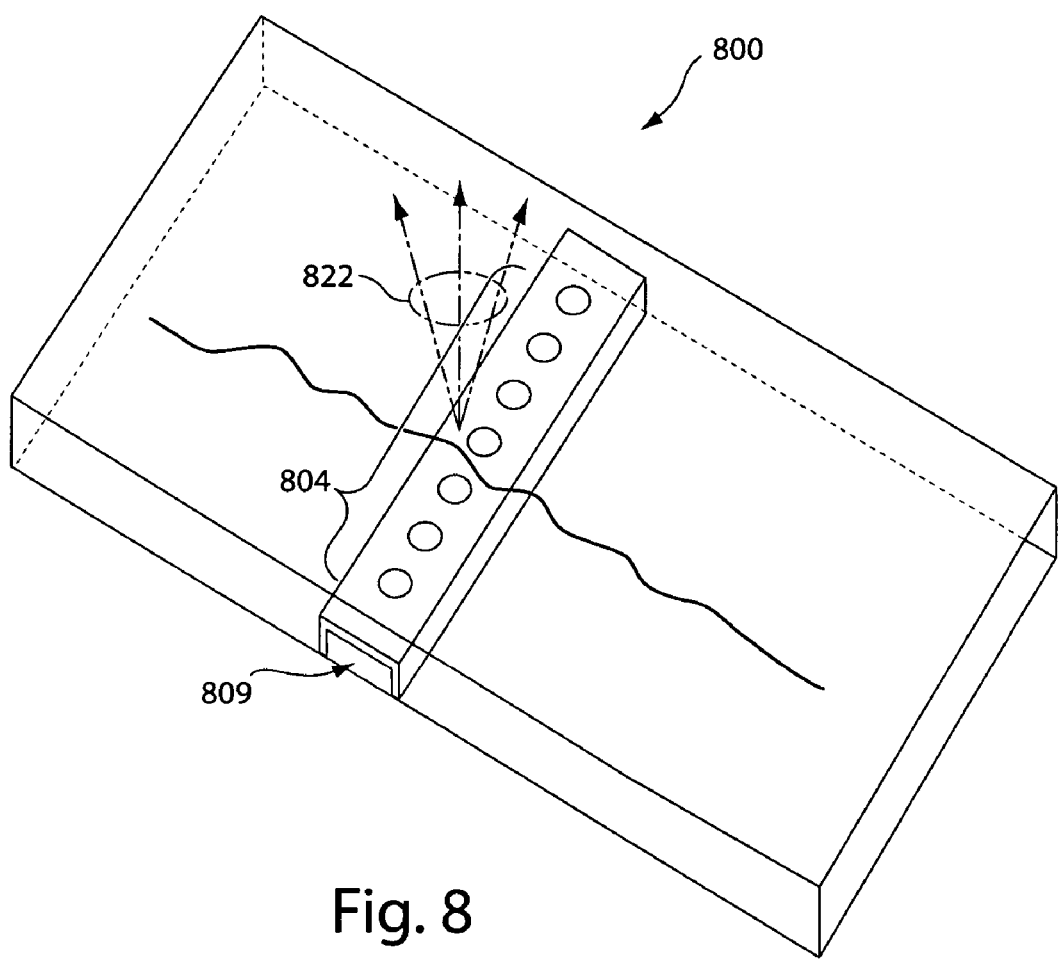
FIG. 8 is a perspective view of a fourth illustrative embodiment of the identification device of FIG. 1 including a second plasmonic resonance-based radiation introduction element, according to an illustrative embodiment of the invention.

FIG. 8 is a perspective view of a fourth illustrative embodiment of the identification device (the "identification device 800") of FIG. 1 including a second plasmonic resonance-based radiation introduction element, according to an illustrative embodiment of the invention. For identification device 800, a radiation introduction element 804 excites plasmonic resonance in a film including a number of preferably periodically spaced holes ("plasmanic arrays"). The holes are excited by laser light passing through an optical waveguide 809 upon which the metal film is disposed. The plasmon resonance frequency of the array of holes is determined by the size and spacing of the holes, as well as the dielectric constant of the surrounding media. The radiation introduction element 804 excites a biomolecule 814 passing over the radiation introduction element 804 into emitting light 822 corresponding to fluorescent tags bound to the biomolecule 814.

Figure 9:
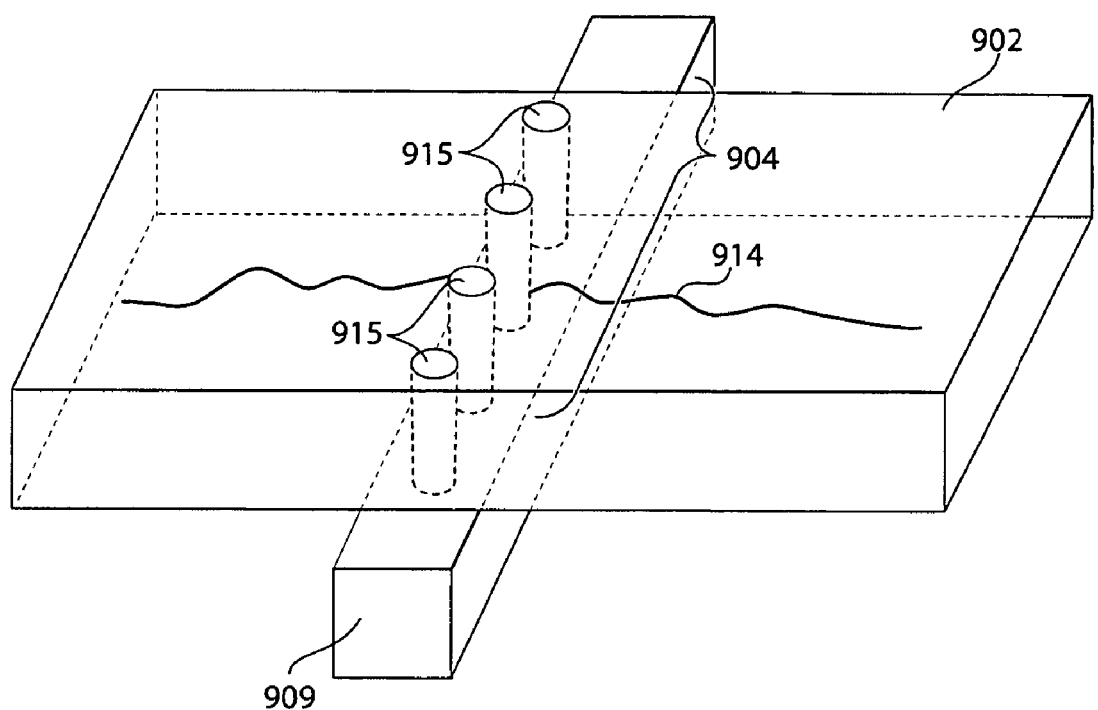
FIG. 9 is a perspective view of a fifth illustrative embodiment of the identification device of FIG. 1 including a third plasmonic resonance-based radiation introduction element, according to an illustrative embodiment of the invention.

FIG. 9 is a perspective view of a third apertureless plasmonic resonance-based radiation introduction element 904, according to an illustrative embodiment of the invention. The radiation introduction element 904 includes a plurality of plasmonic resonant rods 915 (the "rods 915"), spanning from the bottom of a channel 902 of an identification device to the top of the channel 902. Any biomolecule 914 passing through the channel will be forced to pass between a pair of the rods 915, promoting excitation of the biomolecule 914.

The rods 915 may be generally circular, polygonal, or irregular in cross section. The rods 915, in one implementation are spaced periodically across the width of the channel 902. In another implementation, the rods are spaced at different predetermined distances to generate multiple resonant frequencies within the illuminated region of the channel 902. In still another implementation, the radiation introduction element 904 includes multiple rows of rods 915, with each row having a different periodic spacing between pairs of rods 915.

Figure 10:
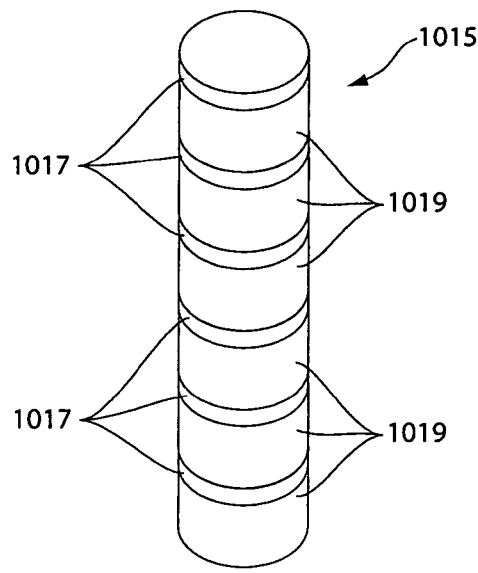
FIG. 10 is a perspective view of a plasmonic resonant rod as may be employed in the identification device of claim 9, according to an illustrative embodiment of the invention.

FIG. 10 is a perspective view of a plasmonic resonant rod 1015 as may be employed in the radiation introduction element 904 of FIG. 9, according to an illustrative embodiment of the invention. To increase the resonance of the rod 1015, the rod is constructed of alternating layers of a dielectric material 1017 and a metal 1019. Referring back to FIG. 9, a radiation introduction element 904 of FIG. 9, including the rods 1015, can be constructed by depositing alternating layers of the materials on top of the waveguide 909. A mask is then applied to the top layer of the deposited materials. Using standard semiconductor processing techniques such as plasma etching or ion-beam milling, the material around the rods 1015 are etched away, leaving the rods 1015 atop the waveguide 909.

Figure 11:
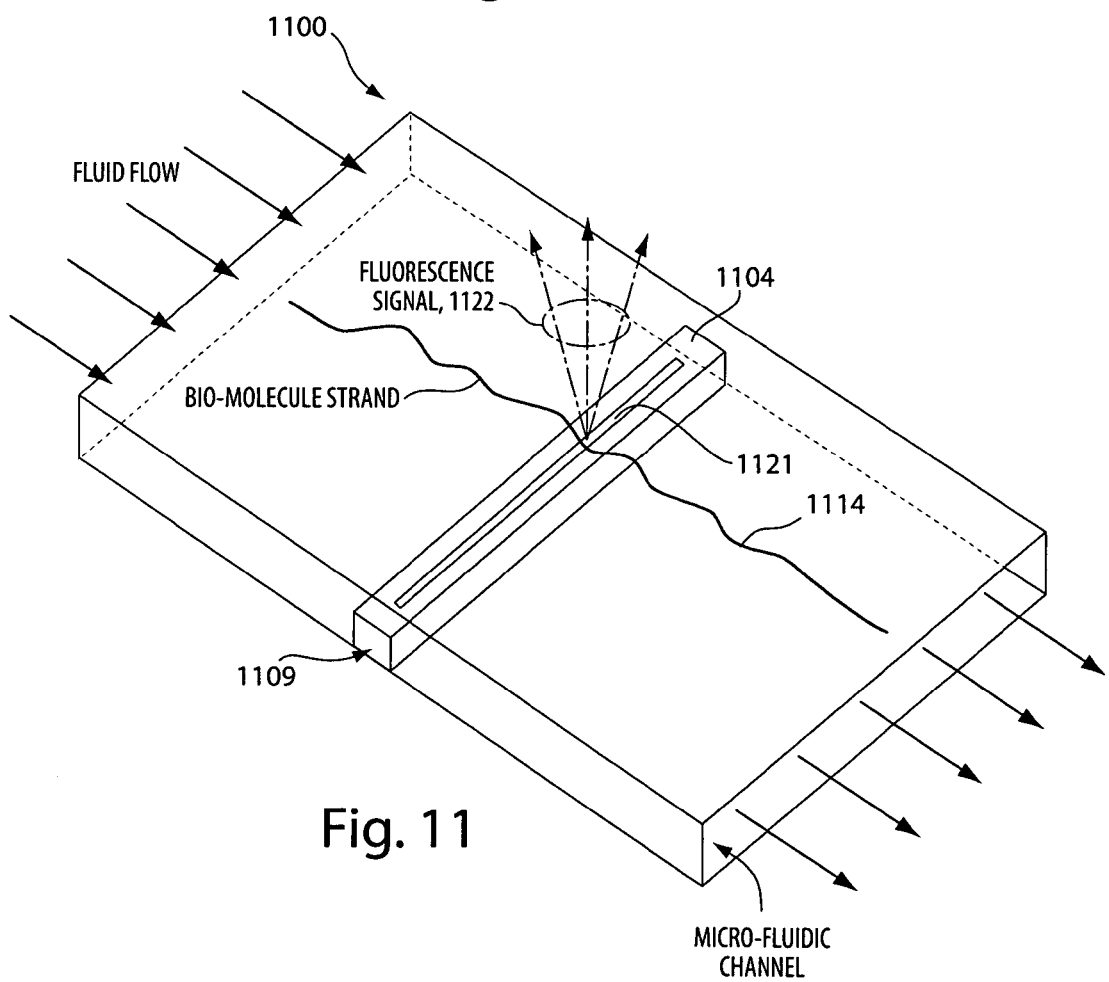
FIG. 11 is a perspective view of a sixth illustrative embodiment of the identification device of FIG. 1 including a fourth apertureless plasmonic resonance-based radiation introduction element, according to an illustrative embodiment of the invention.

FIG. 11 is a perspective view of a sixth illustrative embodiment of the identification device (the "identification device 1100") of FIG. 1 including a fourth apertureless plasmonic resonance-based radiation introduction element, according to an illustrative embodiment of the invention. The identification device 1100 includes a radiation introduction element 1104 that includes a metallic wire 1121, preferably on the order of 10-50 nm wide disposed on an optical waveguide 1109. Laser light passing through the waveguide 1109 excites the wire 1121 into plasmonic resonance, generating an electric field about the wire 1121. The generated electric field excites fluorescent tags bound to passing biomolecules 1114 to emit a distinctive light spectra 1122 corresponding to the tag.

Figure 12A:
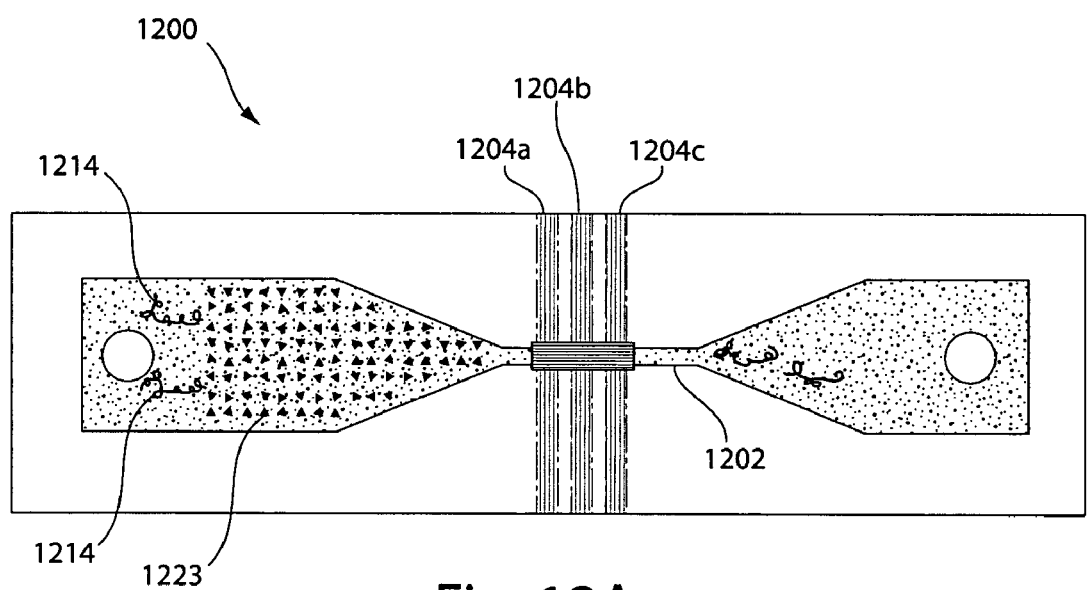
FIG. 12A is a top view of a seventh illustrative embodiment of the identification device of FIG. 1 including a plurality of radiation-introduction elements, according to an illustrative embodiment of the invention.

FIG. 12A is a top view of a seventh illustrative embodiment of the identification device (the "identification device 1200") of FIG. 1, according to an illustrative embodiment of the invention. Identification device 1200 includes three radiation introduction elements 1204a-1204c, The radiation introduction elements 1204a-1204c are separated at predetermined intervals. The identification device 1200 is not limited to only three radiation introduction elements 1204, and can include additional radiation introduction elements spaced at equal or varying intervals along the channel 1202. The device 1200 may be used to identify short biomolecules with multiple tags, by looking for coincident or sequential fluorescence as the tags pass through the radiation introduction elements 1204.

Identification device 1200 also includes a biomolecule barrier region 1223. The biomolecule barrier region 1223 includes a plurality of barriers blocking the channel 1202. The barriers are spaced such that a biomolecule 1214 passing through the barriers would need to be elongated to pass through, preventing bunching up or folding of the biomolecule 1214. The barrier region 1223 may also serve as a filter to prevent clogging of the device.

Figure 12B:
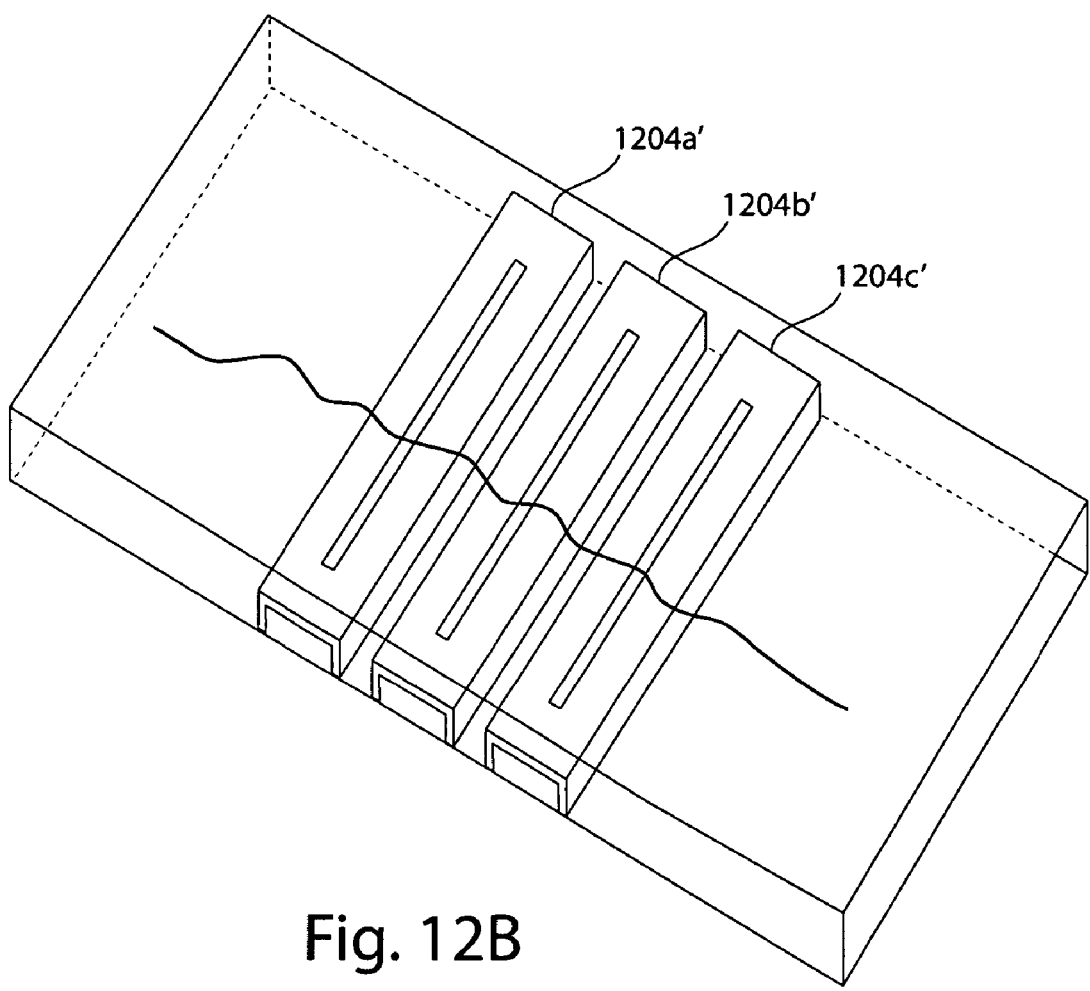
FIG. 12B is a perspective view of a first implementation of the plurality of radiation-introduction elements depicted in FIG. 12A.

FIG. 12B is a perspective view of a first implementation of the plurality of radiation introduction elements 1204a'-1204c' of the identification device 1200 of FIG. 12A. The radiation introduction elements 1204a'-1204c' are of the form depicted in FIG. 3, though each radiation introduction element 1204a'-

1204c' are powered by different wavelength lasers, said wavelengths corresponding to the excitation wavelengths of each fluorescent tag. For example, radiation introduction element 1204a' is powered by a laser emitting red light. Radiation introduction element 1204b' is powered by a laser emitting blue light. Radiation introduction element 1204c' is powered by a laser emitting green light. In an alternative implementation, all three radiation introduction elements 1204a'-1204c' are powered by the same color laser light.

Figure 12C:
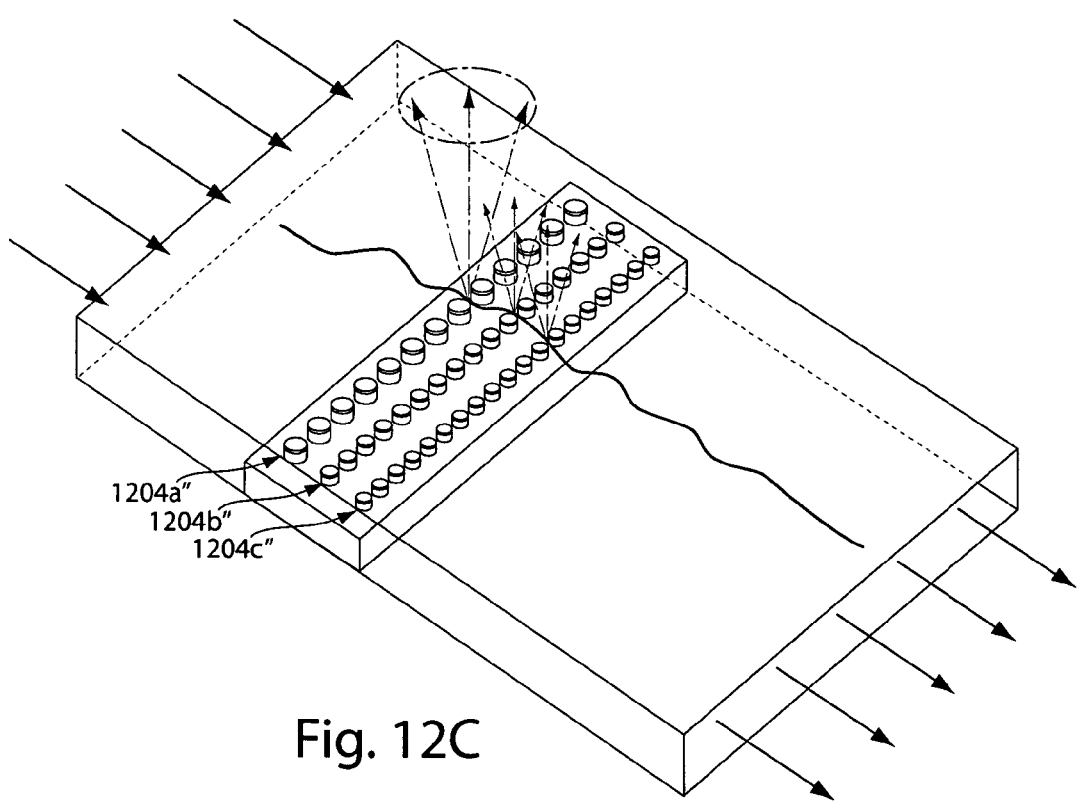
FIG. 12C is a perspective view of a second implementation of the plurality of radiation-introduction elements depicted in FIG. 12A.

FIG. 12C is a perspective view of a second implementation of the plurality of radiation introduction elements 1204a"-1204c" of the identification device 1200 of FIG. 12A. Each of the radiation introduction elements 1204a"-1204c" introduces radiation via plasmonic resonance. In this implementation, for example, the first radiation introduction element 1204a" includes a first linear array of plasmonic resonant elements (such as plasmonic islands or plasmonic rods) 1213" having a first size and a first separation distance, which when excited into resonance excite red fluorescent tags to emit radiation. The second radiation introduction element 1204b", includes a second linear array of plasmonic resonant elements 1213", having a second size and a second separation distance. The second radiation introduction element 1204b" excites emission from green fluorescent tags. The third radiation introduction element 1204c" includes a linear array of plasmonic resonant elements 1213" having a third size and a third separation distances for exciting blue fluorescent tags. Alternatively, the identification device 1200 can include four radiation introduction elements, each tuned to one of four fluorescent tags bound to the bases of a DNA molecules.

The frequency of the electric field between plasmonic resonant elements depends on the size of each element, the spacing of the elements, and the dielectric material upon which the elements are disposed. The appropriate sizes and spacing of the plasmonic resonant elements in each of the radiation introduction islands 1204a"-1204c" can be determined as described in "Electromagnetic Energy Transfer and Switching in Nanoparticle Chain Arrays Below the Diffraction Limit," by M. L. Brongersma et al., in Physical Review B, published on Dec. 15, 2000, and in "Observation of Near-Field Coupling in Metal Nanoparticle Chains Using Far-Field Polarization Spectroscopy," by S. A. Maier et al., in Physical Review B published on May 13, 2002, the entirety of which are hereby incorporated by reference.

Figure 12D:
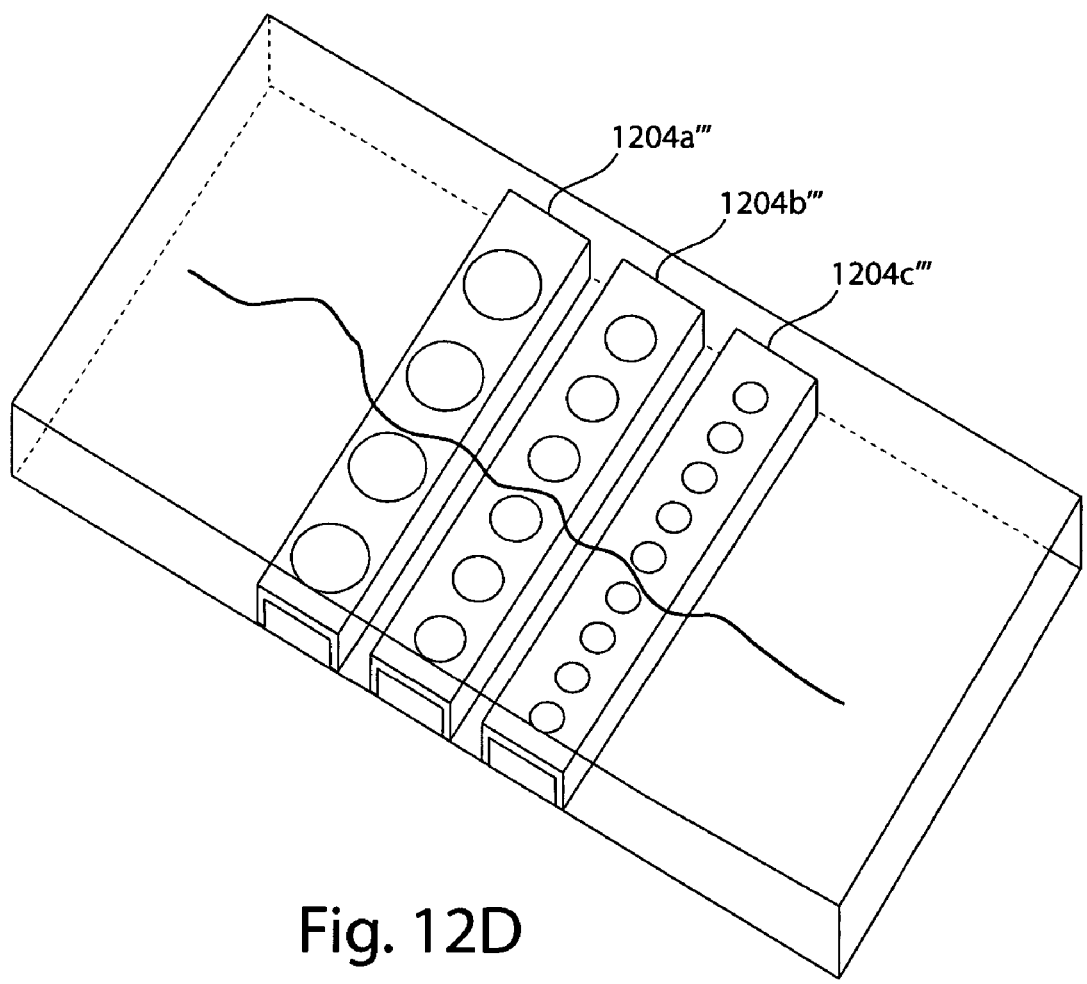
FIG. 12D is a perspective view of a third implementation of the plurality of radiation-introduction elements depicted in FIG. 12A.

FIG. 12D is a perspective view of a third implementation of the plurality of radiation introduction elements 1204a'''-1204c''' of the identification device 1200 of FIG. 12A. The radiation introduction elements 1204a'''-1204c''' incorporate plasmonic resonant arrays as described in relation to FIG. 8. The arrays can be tuned as described above in relation to FIG. 12C.

Figure 13:
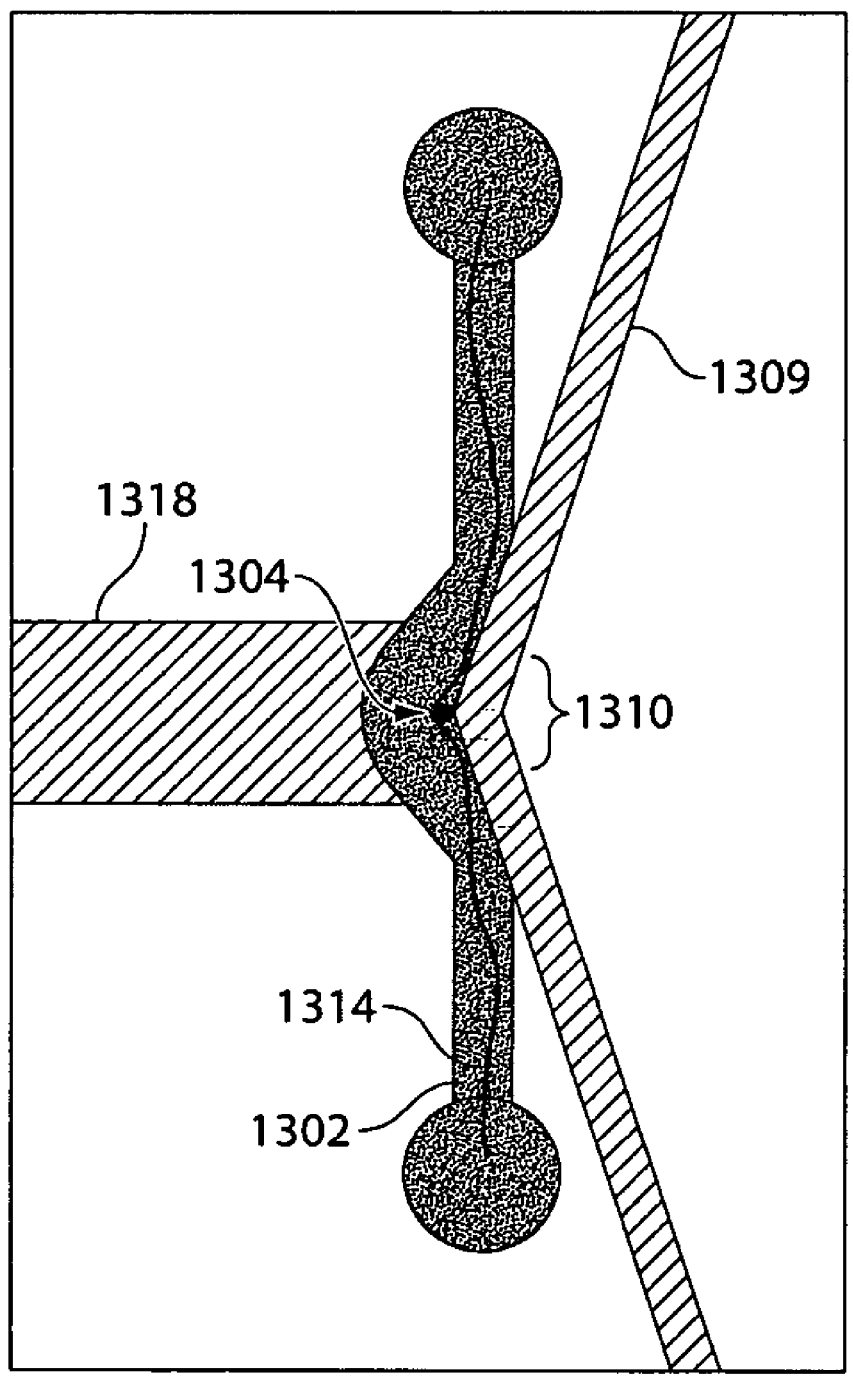
FIG. 13 is a cross sectional view of an eighth illustrative embodiment of the identification device of FIG. 1.

FIG. 13 is a cross sectional view of a portion of an eighth illustrative embodiment of the identification device of FIG. 1 (the "identification device 1300"). As with identification device 100, identification device 1300 includes a channel 1302 through which a biomolecule 1314 is drawn. The channel 1302 includes an indented portion as a positioning element 1310, similar to the shelf positioning element 510 of FIG. 5. However, the positioning element 1310 forms an indent in the channel 1302, as opposed to a shelf. A radiation introduction element 1304, such as an array of plasmonic islands or plasmonic rods, is disposed at the side of the indent. The radiation introduction element 1304 is energized by light passing through a wave guide 1309 running the length of the channel 1302. Light is collected by a second waveguide, light collector 1318, located opposite the indent in the channel 1302.

Figure 14A:
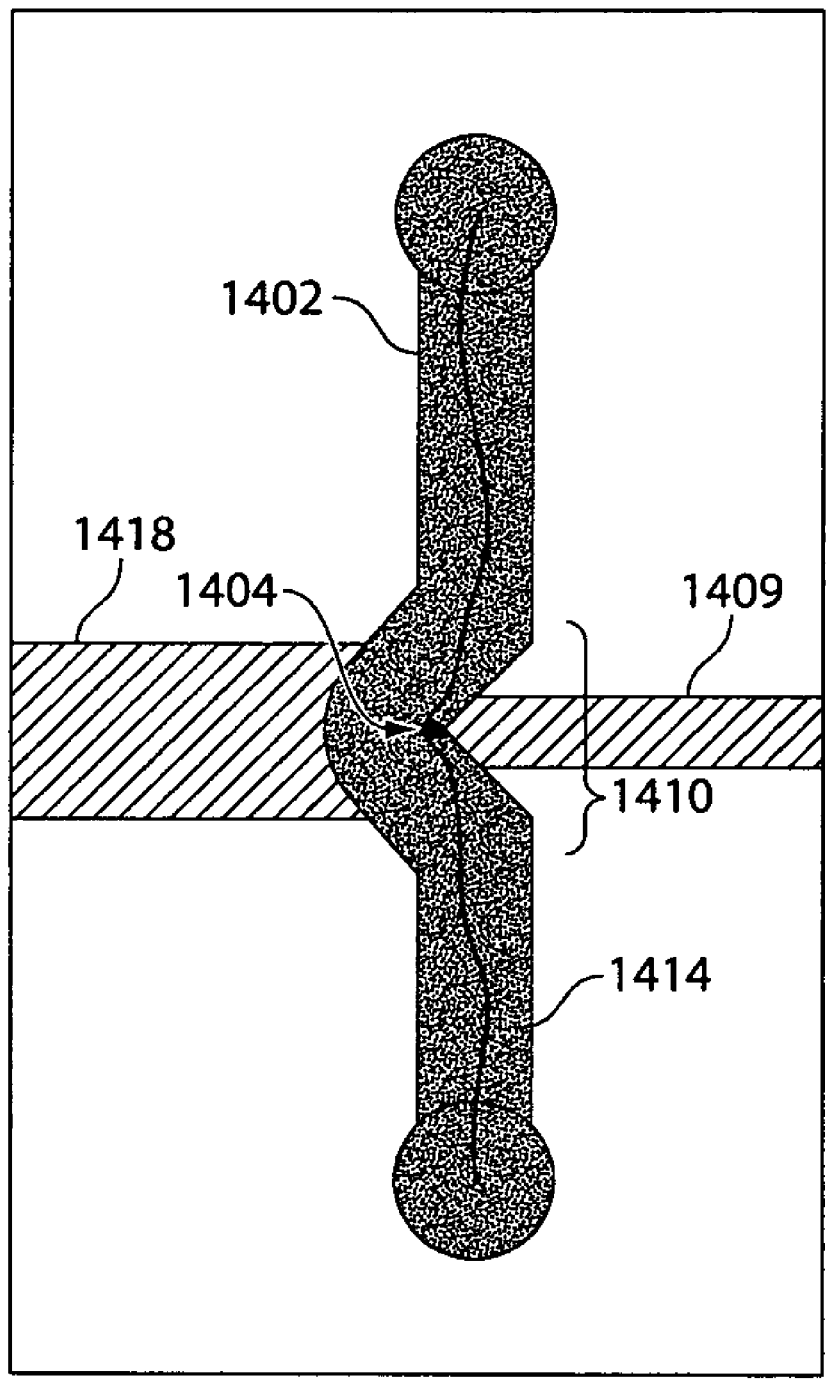
FIG. 14A is a cross sectional view of a ninth illustrative embodiment of the identification device of FIG. 1.

FIG. 14A is a cross sectional view of a portion of a ninth illustrative embodiment of the identification device (the "identification device 1400") of FIG. 1. Like the identification device 1300 of FIG. 13, identification device 1400 includes an indent in a channel 1402, through which a biomolecule 1414 is drawn. The peak serves as a positioning element 1410. A radiation introduction element 1404, such as an array of plasmonic islands or plasmonic rods is disposed at the tip of the indent. The radiation introduction element 1404 is powered by waveguide 1409 located directly below the radiation introduction element 1404. Light emitted from the biomolecule 1414 resulting from the excitation of the biomolecule 1414 by the radiation introduction element 1404 is collected by light collector 1418, in this implementation, another waveguide.

Figure 14B:
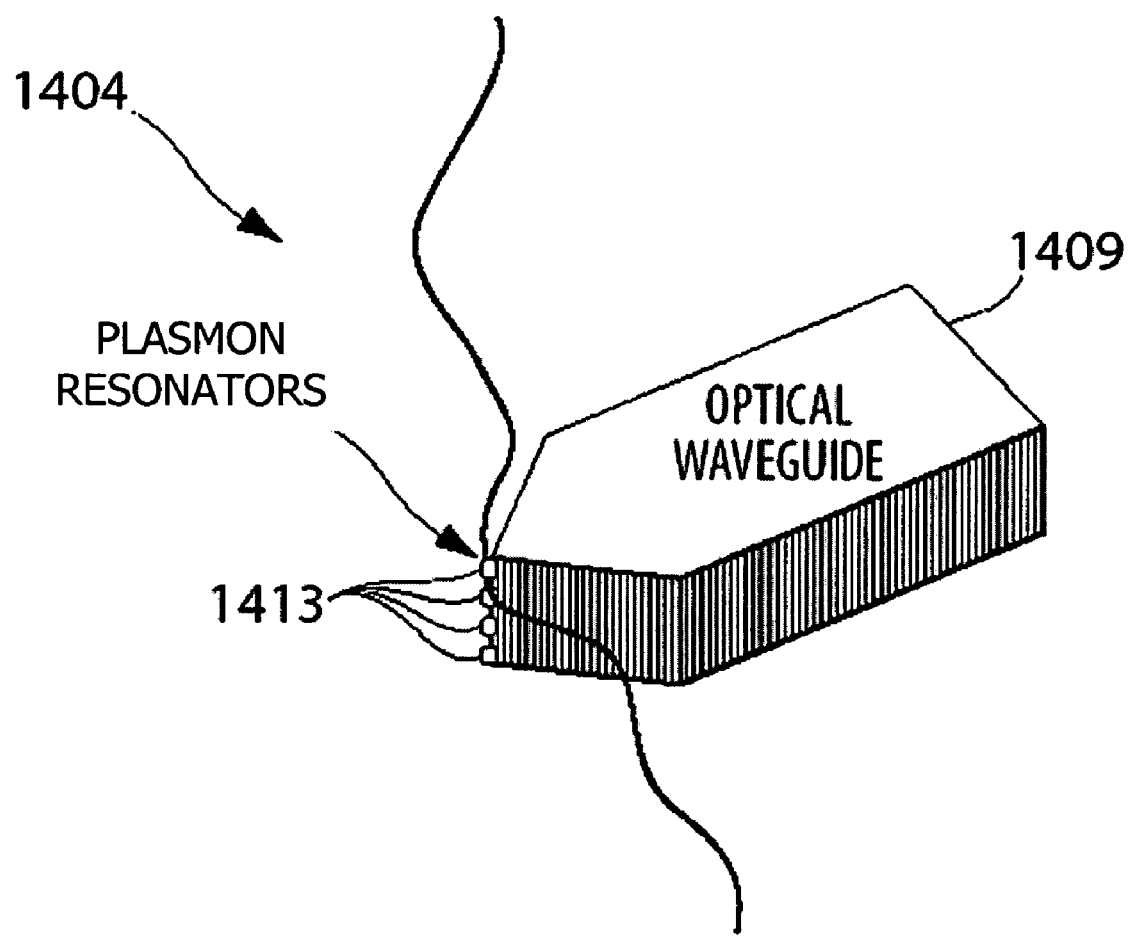
FIG. 14B is a perspective view of a vertical chain of metal nanoparticles incorporated into the radiation introduction element of the identification device of FIG. 4A.

FIG. 14B shows a vertical chain of plasmonic islands 1413 incorporated into the radiation introduction element 1404 of FIG. 14A. These can be formed by attaching metal nanoparticles to the optical waveguide 1409. Alternatively, the plasmonic islands 1413 can be replaced with plasmonic rods such as those described in FIG. 10. The plasmonic rods can be formed by nano-lithography, such as ebeam lithography, and etching of a multilayer stack of alternating metal and dielectric layers. Etching is carried out by plasma etch or ion-beam milling. Lithography is carried out using a suitable photoresist, and e-beam, optical or imprint lithography.

Figure 15:
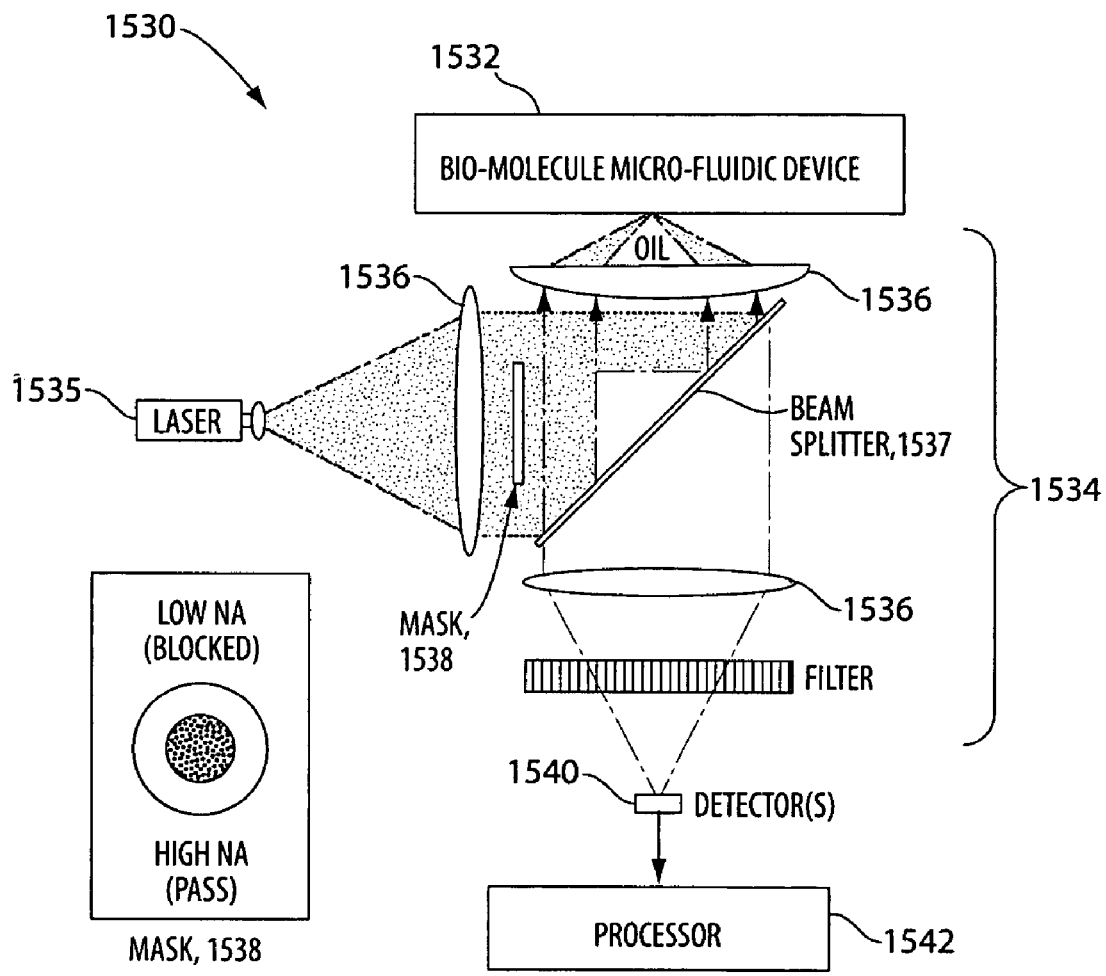
FIG. 15 is a conceptual diagram of an identification system according to an illustrative embodiment of the invention.

FIG. 15 is a conceptual diagram of an identification system 1530 according to an illustrative embodiment of the invention. The identification system 1530 includes elements of the identification devices described above in relation to FIGS. 1, 3, 5, 7-9, and 11-14. For example, with reference to FIG. 1, the identification system 1530 includes a biomolecule microfluidic device 1532 which includes a channel 102 through which a biomolecule 114 is drawn. The biomolecule microfluidic device 1532 also includes a radiation introduction element 104 to excite the biomolecule.

Continuing to refer to FIGS. 1 and 15, the identification system 1530 includes a light guidance portion 1534. The light guidance portion 1534 guides light generated by a laser 1535 into the biomolecule microfluidic device 1532, to power the radiation introduction element 104. The light guidance portion 1534 also guides light collected from the biomolecule microfluidic device 1532 by a light collector 118 resulting from the excitation of the biomolecule to a light detector 120. The light guidance portion 1534 includes a plurality of lenses 1536 and a mask 1538 to block out light at a low numerical aperture and to pass light at a high numeric aperture. The passed light is directed via a beam splitter 1537 into a glass layer adjacent to the fluidic channel in the biomolecule microfluidic device 1532 at an angle resulting in total internal reflection of the light in the glass layer.

Light collected by the light collector 118 passes back through the beam splitter and a filter 1538 to a light detector 1540 (such as light detector 120). In one implementation, the filter 1538 is a band pass filter, only passing light corresponding to the spectra of the fluorescent tags bound to the biomolecule 114. The light detector 1540 communicates the detected light to a processor 1542 (such as processor 106) for analysis and molecule identification.

The invention may be embodied in other specific forms without departing from the spirit or essential characteristics thereof. The forgoing embodiments are therefore to be considered in all respects illustrative, rather than limiting of the invention.

What is claimed is:

1. An identification device comprising:
a channel through which a biomolecule is drawn;

a radiation introduction element accepting light from a light source for introducing electromagnetic radiation into a region of the channel, wherein the region is smaller than the wavelength of light accepted from the light source and wherein the radiation introduction element comprises a plasmonic resonance element;

a sensor for detecting emissions from the biomolecule in the region; and a processor for identifying the biomolecule based on the detected emissions.

2. The identification device of claim 1, wherein the channel is a microfluidic channel.

3. The identification device of claim 1, wherein the emissions from the biomolecule result from the excitation of the biomolecule by the introduced radiation.

4. The identification device of claim 1, comprising:
a set of electrodes for attracting the biomolecule towards the radiation introduction element.

5. The identification device of claim 1, wherein the radiation introduction element includes an aperture having a dimension which is smaller than the wavelength of the light accepted from the light source and the introduced electromagnetic radiation comprises light accepted from the light source.

6. The identification device of claim 5, wherein the dimension of the aperture that is smaller than the wavelength of the light accepted from the light source is a dimension parallel to the channel, and a dimension of the aperture running perpendicular to the channel is substantially larger than the wavelength of the light accepted from the light source.

7. The identification device of claim 5, wherein the plasmonic resonant element comprises a grating positioned about the aperture having a pitch that is less than then the wavelength of the light accepted from the light source.

8. The identification device of claim 1, wherein the radiation introduction element comprises a plurality of plasmonic resonance elements.

9. The identification device of claim 8, wherein the plasmonic resonance elements comprise a linear array of metal islands, wherein the distance between the metal islands is less than the wavelength of the light accepted from the light source.

10. The identification device of claim 9, wherein the spacing between pairs of neighboring plasmonic resonance elements in the linear array varies among the pairs.

11. The identification device of claim 8, comprising a laser as the light source for exciting the plasmonic resonance elements.

12. The identification device of claim 11, wherein the plasmonic resonance elements are coupled to a waveguide, through which the laser excites the plasmonic resonance elements.

13. The identification device of claim 11, wherein the plasmonic resonance elements are optically coupled to a waveguide via an evanescent field, through which the laser excites the plasmonic resonance elements and wherein the introduced radiation comprises an electromagnetic field emanating from the plasmonic resonance elements.

14. The identification device of claim 11, wherein the plasmonic resonance elements comprise a linear array of openings in a metallic strip, wherein the openings are spaced periodically at a distance that is less than the wavelength of the light accepted from the light source.

15. The identification device of claim 11, wherein the plasmonic resonance elements comprise a linear array of metallic rods extending from the bottom of the channel, wherein the biomolecule is drawn between two of the metallic rods as the biomolecule is drawn through the channel.

16. The identification device of claim 15, wherein the metallic rods comprise alternating layers of a conductor and a dielectric.

17. The identification device of claim 1, comprising an output optical wave guide for collecting the emissions from the biomolecule and forwarding the collected emissions to the sensor.

18. The identification device of claim 1, wherein the sensor detects emissions from biomolecules resulting from the excitation of fluorescent tags bound to the biomolecule.

19. The identification device of claim 1, wherein the sensor detects emissions from biomolecules resulting from the excitation of quantum dot tags bound to the biomolecule.

20. The identification device of claim 1, wherein the biomolecule is a strand of DNA, a strand of RNA, or a peptide chain.

21. The identification device of claim 1, comprising a barrier in the channel at about the region for positioning the biomolecule within the region.

22. The identification device of claim 21, wherein the barrier is at least one-half the height of the channel.

23. The identification device of claim 1, wherein said channel comprises a bend perpendicular to the length of the channel at about the region for positioning the biomolecule within the region.

24. The identification device of claim 1, wherein the radiation introduction element is tuned to excite a first spectrum of fluorescence, and wherein the identification device further comprises a second radiation introduction element tuned to excite a second spectrum of fluorescence.

25. The identification device of claim 24, wherein
the radiation introduction element and the second radiation introduction element each include an array of plasmonic resonant elements; and
for each array of plasmonic resonant elements, at least one of a size of the plasmonic resonance elements, a spacing of the plasmonic resonance elements, and a dielectric upon which the plasmonic resonance elements are disposed is selected to tune the arrays of plasmonic resonance elements to their corresponding spectrum of fluorescence.

26. The identification device of claim 1, wherein the introduced electromagnetic radiation comprises an electromagnetic field emanating from the plasmonic resonance element.

27. The identification device of claim 1, wherein the introduced electromagnetic radiation comprises light accepted from the light source.

28. The identification device of claim 1, comprising a waveguide upon which the channel is formed and wherein the plasmonic resonant element is excited into resonance by light introduced into the waveguide.

29. The identification device of claim 28, wherein the plasmonic resonance element comprises a metallic wire disposed on the surface of the waveguide and oriented perpendicular to the length of the channel.

30. The identification device of claim 29, wherein the metallic wire is on the order of 10-50 nm wide.

31. An identification method comprising:
introducing radiation at least in part via a plasmonic resonance element into a region of a channel to generate region smaller than a wavelength of light causing the introduced radiation;
drawing a biomolecule through the region of the channel;
detecting emissions from the biomolecule in the region; and identifying the biomolecule based on the detected emissions.

32. The identification method of claim 31, wherein the channel is a microfluidic channel.

33. The identification method of claim 31, wherein the detected emissions result from the excitation of the biomolecule by the introduced radiation.

34. The identification method of claim 31, comprising energizing a set of electrodes located about the region, thereby attracting the biomolecule towards the region.

35. The identification method of claim 31, wherein the radiation is introduced into the channel via an aperture having a dimension which is smaller than the wavelength of the light.

36. The identification method of claim 35, wherein the dimension of the aperture that is smaller than the wavelength of the light is the dimension parallel to the channel, and the dimension of the aperture running perpendicular to the channel is substantially larger than the wavelength of the light.

37. The identification method of claim 36, wherein the aperture is located within a grating having a pitch that is less than then the wavelength of the light, wherein the grating forms the plasmonic resonance element.

38. The identification method of claim 31, wherein the radiation is introduced into the channel by a plurality of plasmonic resonance elements.

39. The identification method of claim 38, wherein the plasmonic resonance elements comprise a linear array of metal islands, wherein the distance between the metal islands is less than the wavelength of the light.

40. The identification method of claim 39, wherein the spacing between pairs of neighboring plasmonic resonance elements in the linear array varies among the pairs.

41. The identification device of claim 38, wherein the introduced radiation comprises an electromagnetic field and introducing radiation into the channel comprises exciting the plasmonic resonance elements with a laser.

42. The identification device of claim 41, wherein the introduced radiation comprises an electromagnetic field and introducing radiation into the channel comprises exciting the plasmonic resonance elements with a laser via an evanescent field.

43. The identification device of claim 41, wherein the laser excites the plasmonic resonance elements by passing laser light through a waveguide to which the plasmonic resonance elements are coupled.

44. The identification method of claim 38, wherein the plasmonic resonance elements comprise a linear array of openings in a metallic strip and wherein the openings are spaced periodically at a distance that is less than the wavelength of the light.

45. The identification method of claim 38, wherein the plasmonic resonance elements comprise a linear array of metallic rods extending from the bottom of the channel, and wherein the biomolecule is drawn between two of the metallic rods as the biomolecule is drawn through the channel.

46. The identification device of claim 45, wherein the metallic rods comprise alternating layers of a conductor and a dielectric.

47. The identification method of claim 31, wherein the sensor detects emissions from biomolecules resulting from the excitation of fluorescent tags bound to the biomolecule.

48. The identification method of claim 31, wherein the sensor detects emissions from biomolecules resulting from the excitation of quantum dot tags bound to the biomolecule.

49. The identification method of claim 31, wherein the biomolecule is a strand of DNA, a strand of RNA, or a peptide chain.

50. The identification method of claim 31, comprising providing a barrier in the channel at about the illuminated region for positioning the biomolecule within the region.

51. The identification method of claim 50, wherein the barrier is at least one-half the height of the channel.

52. The identification method of claim 31, wherein said channel comprises a bend perpendicular to the length of the channel at about the region for positioning the biomolecule within the region.

53. The identification method of claim 31, comprising collecting the emissions from the biomolecule via an output optical wave guide and forwarding the collected emissions to the sensor.

54. The identification method of claim 31, wherein the introduced radiation is tuned to excite a first spectrum of fluorescence, the method further comprising introducing a second radiation tuned to excite a second spectrum of fluorescence.

55. The identification method of claim 54, wherein
the introduced radiation and the second introduced radiation are generated in part by respective arrays of plasmonic resonant elements; and
for each array of plasmonic resonant elements, at least one of a size of the plasmonic resonant elements, a spacing of the plasmonic resonant elements, and a dielectric upon which the plasmonic resonant elements are disposed is selected to tune the array of plasmonic resonant elements to its corresponding spectrum of fluorescence.

56. The identification method of claim 31, wherein the introduced radiation comprises an electromagnetic field emanating from the plasmonic resonance element.

57. The identification method of claim 31, wherein the introduced electromagnetic radiation comprises a portion of the light.

58. A microfluidic apparatus for use in an identification device comprising:
a channel through which a biomolecule is drawn; and
a radiation introduction element for accepting light from a light source for introducing electromagnetic radiation into a region of the channel, wherein the region is smaller than the wavelength of the light accepted from the light source and wherein the radiation introduction element comprises a plasmonic resonance element.

* * * * *